United States Patent
Liu et al.

(10) Patent No.: US 10,801,934 B2
(45) Date of Patent: Oct. 13, 2020

(54) ROCK MECHANICS EXPERIMENT SYSTEM FOR SIMULATING DEEP-UNDERGROUND ENVIRONMENT

(71) Applicants: Sichuan University, Chengdu (CN); Research Institute of Petroleum Exploration & Development, PetroChina Company Limited, Beijing (CN)

(72) Inventors: Jianfeng Liu, Chengdu (CN); Guosheng Ding, Beijing (CN); Zhide Wu, Beijing (CN); Qiqi Wanyan, Beijing (CN); Lina Ran, Beijing (CN); Jianliang Pei, Chengdu (CN); Lu Wang, Chengdu (CN); Huining Xu, Chengdu (CN); Chunping Wang, Chengdu (CN); Yilin Liao, Chengdu (CN); Qiangxing Zhang, Chengdu (CN); Xiaozhang Lei, Chengdu (CN); Wenxi Fu, Chengdu (CN); Min Zhang, Beijing (CN)

(73) Assignees: SICHUAN UNIVERSITY, Chengdu (CN); RESEARCH INSTITUTE OF PETROLEUM EXPLORATION & DEVELOPMENT, PETROCHINA COMPANY LIMITED, Beijing (CN)

( * ) Notice: Subject to any disclaimer, the term of this patent is extended or adjusted under 35 U.S.C. 154(b) by 140 days.

(21) Appl. No.: 16/036,899

(22) Filed: Jul. 16, 2018

(65) Prior Publication Data
US 2018/0340874 A1  Nov. 29, 2018

(30) Foreign Application Priority Data
May 15, 2017 (CN) .......................... 2017 1 0339853

(51) Int. Cl.
*G01N 3/12* (2006.01)
*G01N 3/18* (2006.01)
*G01N 33/24* (2006.01)

(52) U.S. Cl.
CPC ................. *G01N 3/12* (2013.01); *G01N 3/18* (2013.01); *G01N 33/24* (2013.01);
(Continued)

(58) Field of Classification Search
CPC .. G01N 3/12; G01N 3/18; G01N 3/06; G01N 3/10; G01N 33/24
See application file for complete search history.

(56) References Cited

U.S. PATENT DOCUMENTS 3,182,493 A * 5/1965 Patterson ................. G01N 3/08
                                                              73/831
3,354,704 A * 11/1967 Gloor ....................... G01N 3/16
                                                              73/796

(Continued)

*Primary Examiner* — Helen C Kwok
(74) *Attorney, Agent, or Firm* — Bayramoglu Law Offices LLC

(57) ABSTRACT

The present invention discloses a rock mechanics experiment system for simulating deep-underground environment, including a triaxial chamber consisting of a chamber cavity and a test pedestal, a stress field building module, a high pressure seepage field building module, a high temperature field building and a seepage medium permeating control measurement module arranged in the triaxial chamber, a lifting module used for installing and disassembling of the chamber cavity, and computer module used for controlling the operation of system and calculating and outputting the test data. The lifting module includes a door-shaped support frame, a cylinder piston device vertically mounted on the door-shaped support frame beam, a coupling device and a safety suspension device. The coupling device includes an oil hydraulic rod with the upper end fixedly coupled with the piston, a safety disk fixedly coupled with the lower end of (Continued)

the hydraulic rod, and two symmetrically disposed coupling assemblies.

20 Claims, 5 Drawing Sheets

(52) U.S. Cl.
CPC ............... *G01N 2203/0019* (2013.01); *G01N 2203/0048* (2013.01); *G01N 2203/0226* (2013.01); *G01N 2203/0232* (2013.01)

(56) References Cited

U.S. PATENT DOCUMENTS

| | | | | |
|---|---|---|---|---|
| 9,488,559 B2* | 11/2016 | Liu | ........................ | G01N 3/04 |
| 9,488,560 B2* | 11/2016 | Liu | ........................ | G01N 3/08 |
| 9,500,574 B2* | 11/2016 | Liu | ........................ | G01N 3/08 |
| 9,714,891 B2* | 7/2017 | Liu | ........................ | G01N 3/10 |
| 2018/0340874 A1* | 11/2018 | Liu | ........................ | G01N 3/12 |
| 2019/0331568 A1* | 10/2019 | Liu | ........................ | G01N 3/10 |
| 2019/0331570 A1* | 10/2019 | Liu | ........................ | G01N 3/12 |

* cited by examiner

ROCK MECHANICS EXPERIMENT SYSTEM FOR SIMULATING DEEP-UNDERGROUND ENVIRONMENT

CROSS REFERENCE TO RELATED APPLICATIONS

This application is based upon and claims priority to Chinese Patent Application No. CN201710339853.1, filed on May 15, 2017, the entire content of which is incorporated herein by reference.

TECHNICAL FIELD

The present invention relates to the field of rock test piece mechanics experiments in geological environment research, in particular to a rock mechanics experiment system for simulating deep-underground environment.

BACKGROUND

The deep-underground rock mass is in the environment of high temperature field, high pressure seepage field and high in-situ stress field and sometimes, it is affected by the presence of chemical substances, such as carbon dioxide injected into the deep underground, i.e. the deep-underground rock mass is in the environment under the effect of various field environments such as heat, force, water, gas and chemicals, etc. The mechanics experiment system that simultaneously simulates environmental conditions such as high temperature field, high pressure seepage field, high in-situ stress field, and the presence of chemical substances in the deep underground is a necessary condition to carry out research on rock mechanical behaviors under real environmental conditions of deep rock masses.

In the deep geological environment condition, the deeper we go underground, the higher will be the temperature and in-situ stress. When the depth reaches 7000 m, the horizontal in-situ stress estimated by the vertical self-weight stress can reach above 200 MPa and the temperature can reach above 200° C. Currently, in the rock mechanics experiment for simulating deep-underground environment, as the simulated deep temperature and horizontal in-situ stress are higher, the triaxial pressure chamber as the main test equipment is larger and heavier. When the confining pressure under triaxial stress reaches 200 MPa and the temperature reaches 200° C., the adopted self-balancing triaxial pressure chamber (called as triaxial chamber for short) has a cavity diameter of about 0.7 meters, a height of about 1.4 meters, and a weight of about 2 tons. A piston used as an axial loading actuator in the triaxial chamber is located at the upper part of the center of the triaxial chamber and moves telescopically inside the triaxial chamber along the central axis of the triaxial chamber. A piston rod penetrates through the top end of the triaxial chamber cavity. A guide rod of an axial displacement deformation sensor for measuring the deformation of the test piece passes through the piston used as the axial loading actuator and the top end of the triaxial chamber cavity along the central axis of the triaxial chamber, and the length of the guide rod is 70 cm. To install the test piece inside the triaxial chamber or remove the test piece from the triaxial chamber, first the guide rod is needed to be removed from the top of the triaxial chamber, then all of fixing bolts installing the chamber cavity on a test pedestal are dismantled, and then the chamber cavity of the triaxial chamber is lifted upward by 0.8 meters to one side and the chamber cavity is dropped on the ground slowly. Since there are only two small bolt holes at the top of the chamber cavity which can be connected for lifting, and the chamber cavity is large in size and heavy in weight, a soft lifting belt should pass through the two bolt holes and then be hung on a hook of a manual lifting hoist when lifting. The manual hoist is arranged on a beam of a bracket of a gantry structure with a roller at the bottom, and then a chain of the lifting hoist is pulled by an experimenter manually to lift the chamber cavity. After the chamber cavity is lifted to a predetermined height, a gantry is pushed away from a base of the triaxial chamber, and then the chamber cavity drops onto the ground. After the test piece to be tested is installed on the test pedestal of the triaxial chamber, the chamber cavity is lifted to the predetermined height, then the gantry hung with the chamber cavity is pushed right above the test pedestal of the triaxial chamber where the test piece is installed, and the chain of the lifting hoist is manually pulled to lower the chamber cavity to a predetermined position of the test pedestal of the triaxial chamber.

According to the experiment system of the prior art, during the operation of placing the rock test piece inside the triaxial chamber and removing the rock test piece from the triaxial chamber, not only many operators are required to complete the experiment, but also there are many links and hidden dangers in the process. Firstly, the triaxial chamber cavity is large in size and heavy in weight, at least four people are required to barely complete lifting and lowering process. In order to ensure the stability of the chamber cavity in the process of lifting and lowering, several operators are required to apply force by hand to maintain the chamber cavity balance. If the chamber cavity swings during lifting, not only the operators lifting the chamber cavity may disbalance, but also some danger may be caused to the operators who use hands to apply thrust to maintain the chamber cavity balance. Secondly, during lifting, since the chamber cavity is hung on the hook through the soft belt, it cannot be ensured that the direction of the center of gravity of the pressure chamber cavity coincides with the central axis of the triaxial chamber during lifting. During lifting and lowering process of the chamber cavity, the test piece installed inside the triaxial chamber may be damaged or even a loading indenter may be knocked off due to a slight mistake, which may also cause injury to the operators. Thirdly, due to the large weight of the chamber cavity, the direction of the center of gravity of the chamber cavity during lifting and lowering does not coincide with the axis of the pressure chamber, which may damage the seal ring with high temperature resistance and high pressure resistance on the test pedestal during lowering, so the experiment cannot be carried out. Fourthly, because the manual hoist is used for lifting and lowering, the chain may get stuck and the chamber body may get suspended in the air during lifting and lowering. It is troublesome to repair the manual hoist to lift and lower normally. The inadvertent operation in the repair process will not only cause damage to the entire experiment system, but also may cause serious personal injury. Fifthly, when the chamber cavity is lifted to the predetermined height to be removed from the top of the base or moved from the side of a test machine to the top of the base of the pressure chamber where the test piece is installed, the chamber cavity suspended in the air may swing when the gantry is pushed, which causes unsafe psychological impact on the experimenter. Sixthly, the area of the laboratory is relatively small, if the triaxial chamber cavity is removed from the base of triaxial chamber of the test machine and placed on the ground of the laboratory, other preparations before the test will be extremely inconvenient.

SUMMARY

In view of the shortcomings of the existing rock mechanics experiment system, the present invention provides a rock mechanics experiment system for simulating deep-underground environment, so as to solve the problems that the chamber cavity of the rock mechanics experiment system in the prior art is difficult to install and disassemble and poses great security risks during the experiment.

The rock mechanics experiment system for simulating deep-underground environment provided by the present invention includes a triaxial chamber consisting of a chamber cavity and a test pedestal, a stress field building module, a high pressure seepage field building module and a high temperature field building module inside the triaxial chamber, a seepage medium permeating measurement and controlling module, a lifting module used for installing and disassembling the chamber cavity, and a computer measurement and controlling module. The lifting module includes a door-shaped support frame, a cylinder piston device vertically installed on a beam of the door-shaped support frame, a coupling device and a safety suspension device. The coupling device include an oil hydraulic rod with the upper end fixedly connected to a piston, a safety disk fixedly connected to the lower end of the oil hydraulic rod, and two coupling assemblies arranged symmetrically with the upper ends fixedly connected to the safety disk and the lower ends fixedly connected to the upper end of the chamber cavity, each of the coupling assemblies consists of an upper lifting rod with the upper end fixedly connected to the safety disk, a lower lifting rod with the lower end fixedly connected to the upper end of the chamber cavity and a locking pin. The lower end of the upper lifting rod and the upper end of the lower lifting rod are connected through the locking pin in a socket way. The safety suspension device includes four fixing rods and two locking pin rods, the four fixing rods are fixed on the beam of a door-shaped support frame through upper ends and are arranged opposite to one another in pairs. The lower end of each fixing rod is designed with a locking pin hole matched with the locking pin rod in the socket way. The two locking pin rods are respectively inserted into the locking pin holes on lower end parts of the two fixing rods oppositely arranged and are axially fixed, and the four fixing rods and the two locking pin rods form a hanging and carrying frame for suspending the safety disk.

In the above-mentioned technical solution of the present invention, the four fixing rods forming the hanging and carrying frame for suspending the safety disk can be fixed under the beam of the door-type support frame opposite one another in pairs, or can be fixed on the two side surfaces of the beam of the door-type support frame opposite one another in pairs, and the latter installation method is preferentially selected.

In the above-mentioned technical solution of the present invention, in order to prevent the failure of the hanging and carrying frame consisting of four fixing rods and two locking pin rods, the locking pin rod can be designed to be long enough, or an axial positioning structure can be designed on the locking pin rod to prevent the locking pin rod from moving axially. The second method is preferentially selected. The axial positioning structure can be an external thread with a fixed end cap at one end and the other end forming a thread pair with the nut, or a socket pair formed with a transverse locking pin; the axial positioning structure can also be an external thread with both ends forming thread pairs with the nuts, or a socket pair formed with transverse locking pin. As long as the locking pin rods can be prevented from sliding out of the locking pin holes oppositely arranged at the lower ends of the two fixing rods, the external thread with both ends forming thread pair fixing structures with the nuts at both ends of the locking pin rod is preferably used for axial fixing.

In the above-mentioned technical solution of the present invention, a coupling chassis can be fixedly arranged at the upper end of the chamber cavity, the coupling chassis is provided with an installation hole sleeved with an axial loading piston shaft, the lower end of the lower lifting rod in the coupling assembly is fixedly connected with the coupling chassis, and the lower lifting rod is fixedly connected to the upper end of the chamber cavity through the coupling chassis. The way that the lower end of the lower lifting rod is fixedly connected to the coupling chassis can be by welding or a thread pair connection.

In the above-mentioned technical solution of the present invention, the distance of the rising stroke of the piston of the cylinder piston device is more than 0.40 meters, so that it is convenient for the test piece to be installed on and removed from the test pedestal.

In the above-mentioned technical solution of the present invention, the hydraulic oil control switch of the cylinder piston device is preferably arranged on a conveying pipe positioned on a vertical frame of the door-shaped support frame.

In the above-mentioned technical solution of the present invention, the stress field building module includes an axial stress field loading measurement and controlling module and a lateral stress field loading measurement and controlling module. The high pressure seepage field building module includes a liquid seepage field building loading measurement and controlling module and a gas seepage field building loading measurement and controlling module. The seepage medium permeating measurement and controlling module includes a seepage liquid permeating measurement and controlling module and a seepage gas permeating measurement and controlling module. The liquid seepage field building loading measurement and controlling module and the gas seepage field building loading and controlling module share one seepage medium inlet connection pipe, and the seepage liquid permeating measurement and controlling module and the seepage gas permeating measurement and controlling module share one outlet connection pipe.

The rock mechanics experiment system for simulating deep-underground environment provided by the present invention can realize mechanical experiments on the rock test piece by simulating the environmental conditions of deep-underground high temperature field, the high pressure seepage field, the high in-situ stress field and the presence of chemical media in one self-balancing pressure triaxial chamber respectively or in combination, solving the problem where mechanical experiments on rock test piece cannot be carried out under different environmental conditions at the same time in one self-balancing pressure triaxial chamber in the prior art. In particular, the lifting module specially designed by the present invention for installing and disassembling the chamber cavity solves the difficult problem of the prior art, where the coincidence of the direction of the center of gravity of the chamber cavity of the pressure chamber and the central axis of the triaxial chamber cannot be ensured during lifting due to the large size and heavy weight of the chamber cavity so that multiple persons are required to complete the installation and disassembly of the chamber cavity, and a great hidden danger to the personal safety of the experimenter exists, in the installation and disassembly operation process, the experimenters need to be extremely cautious, and test piece installed in the triaxial chamber may be crashed, even the loading indenter may be knocked off, or the seal ring with high temperature resistance and high pressure resistance on the base may be damaged due to a slight mistake, and more importantly, the lifting module solves the difficult problem that the guide rod of the axial displacement deformation sensor for measuring the deformation of the test piece is convenient to install and disassemble before and after the test. The lifting module for installing and disassembling the chamber cavity of the present invention can keep the chamber cavity moving vertically up and down in the process of lifting and dropping through the coupling device and the safety suspension device which have ingenious structure designs. The axis of the chamber cavity is positioned on the axis of the triaxial chamber, the chamber cavity can be safely suspended on the beam of the door-shaped support frame right above the triaxial chamber installation seat after being lifted by a certain height, and a experimenter can install the rock test piece inside the triaxial chamber or remove the rock test piece from the triaxial chamber conveniently, thereby eliminating the hidden danger to the personal safety of the experimenter caused by the swing of the chamber cavity in the installation and disassembly process of the existing test system and realizing the convenient installation and disassembly of the guide rod of the axial displacement deformation sensor for measuring the deformation of the test piece before and after the test at the same time.

Figure 1:
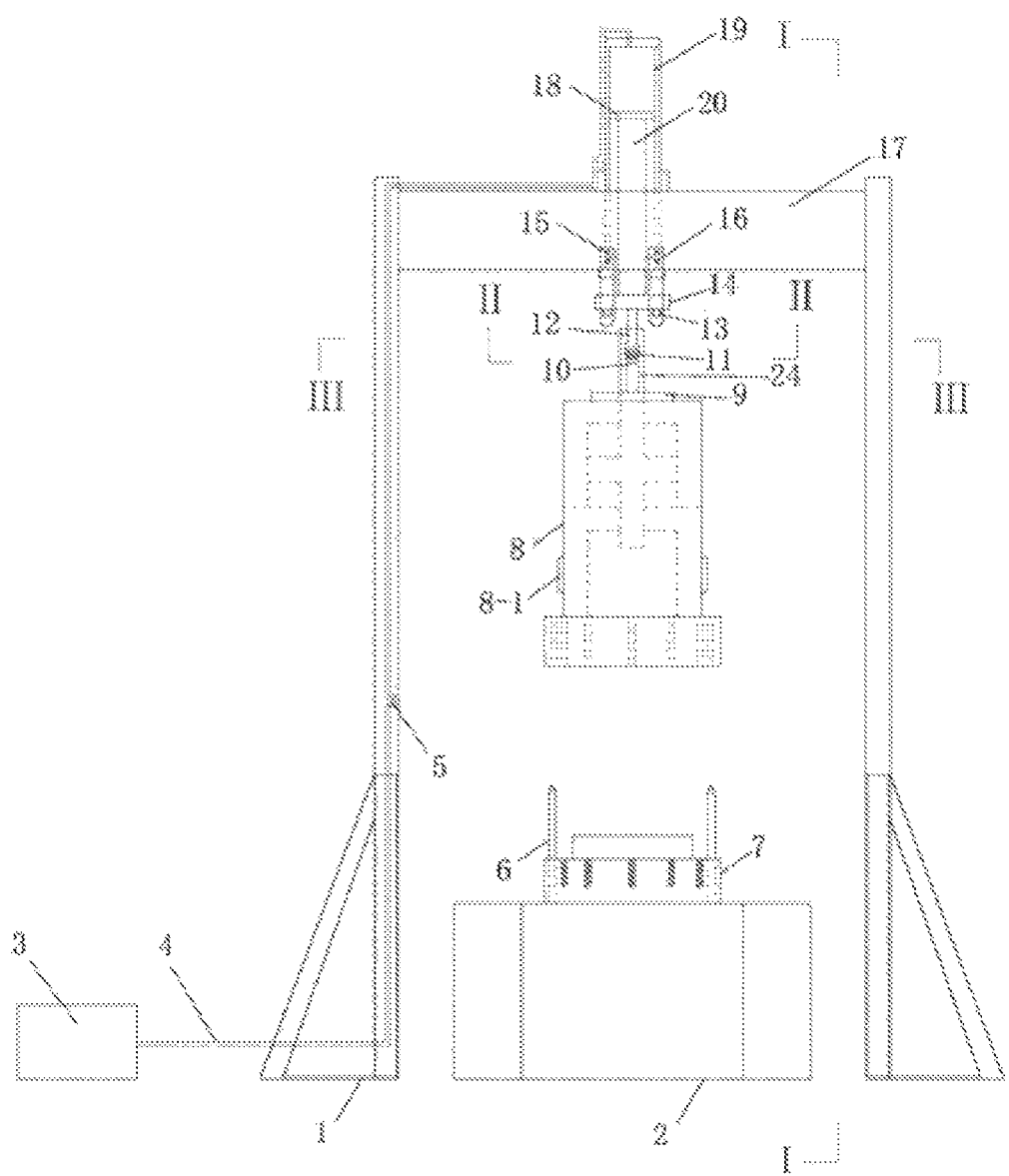
FIG. 1 is a structural diagram of a front view of a lifting module used for installing and disassembling of chamber cavity of the present invention.
Figure 2:
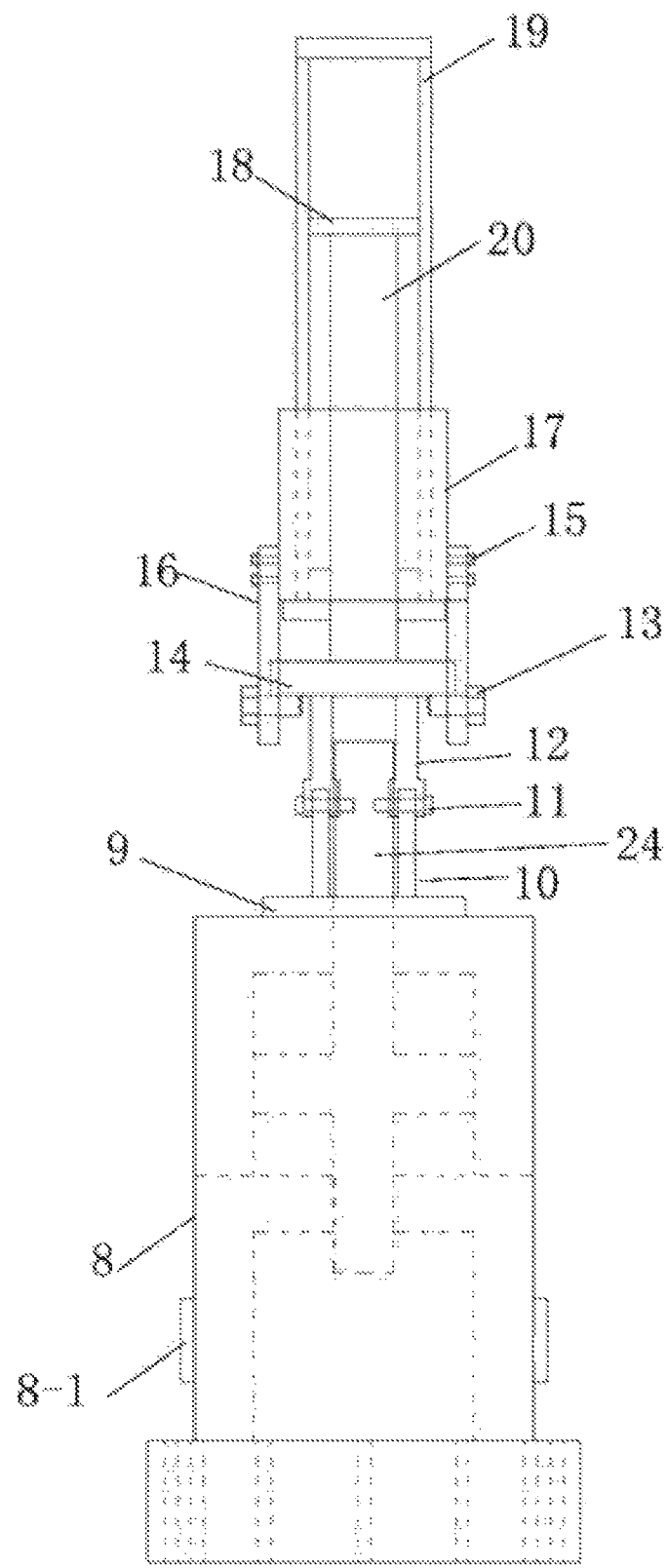
FIG. 2 is a structural diagram of a bottom view of I-I direction in FIG. 1.
Figure 3:
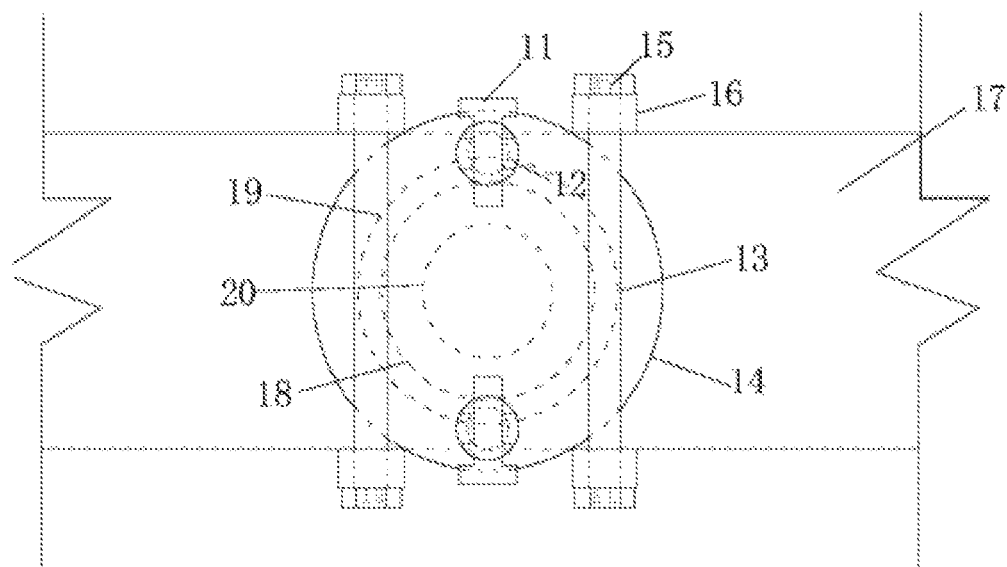
FIG. 3 is a structural diagram of a bottom view of II-II direction in FIG. 1.
Figure 4:
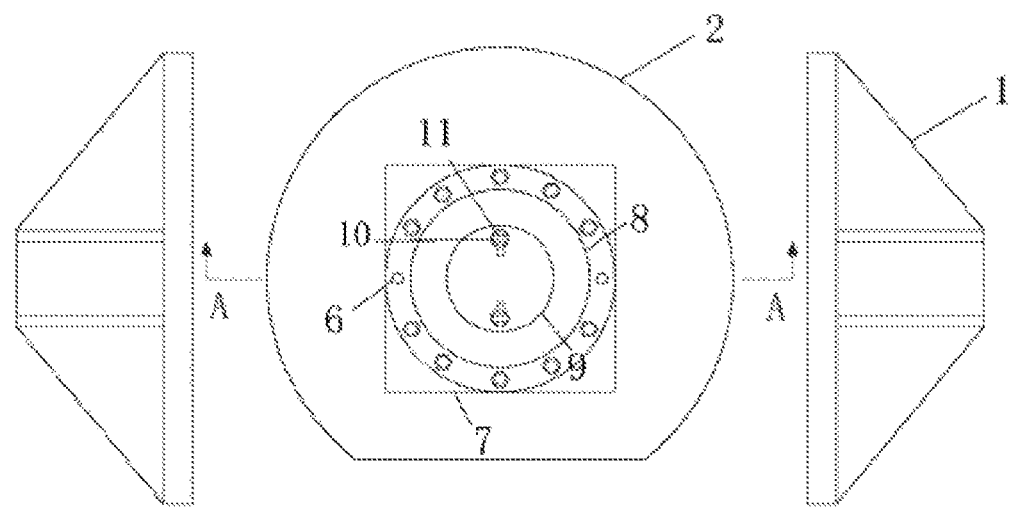
FIG. 4 is a structural diagram of a top view of direction in FIG. 1.
Figure 5:
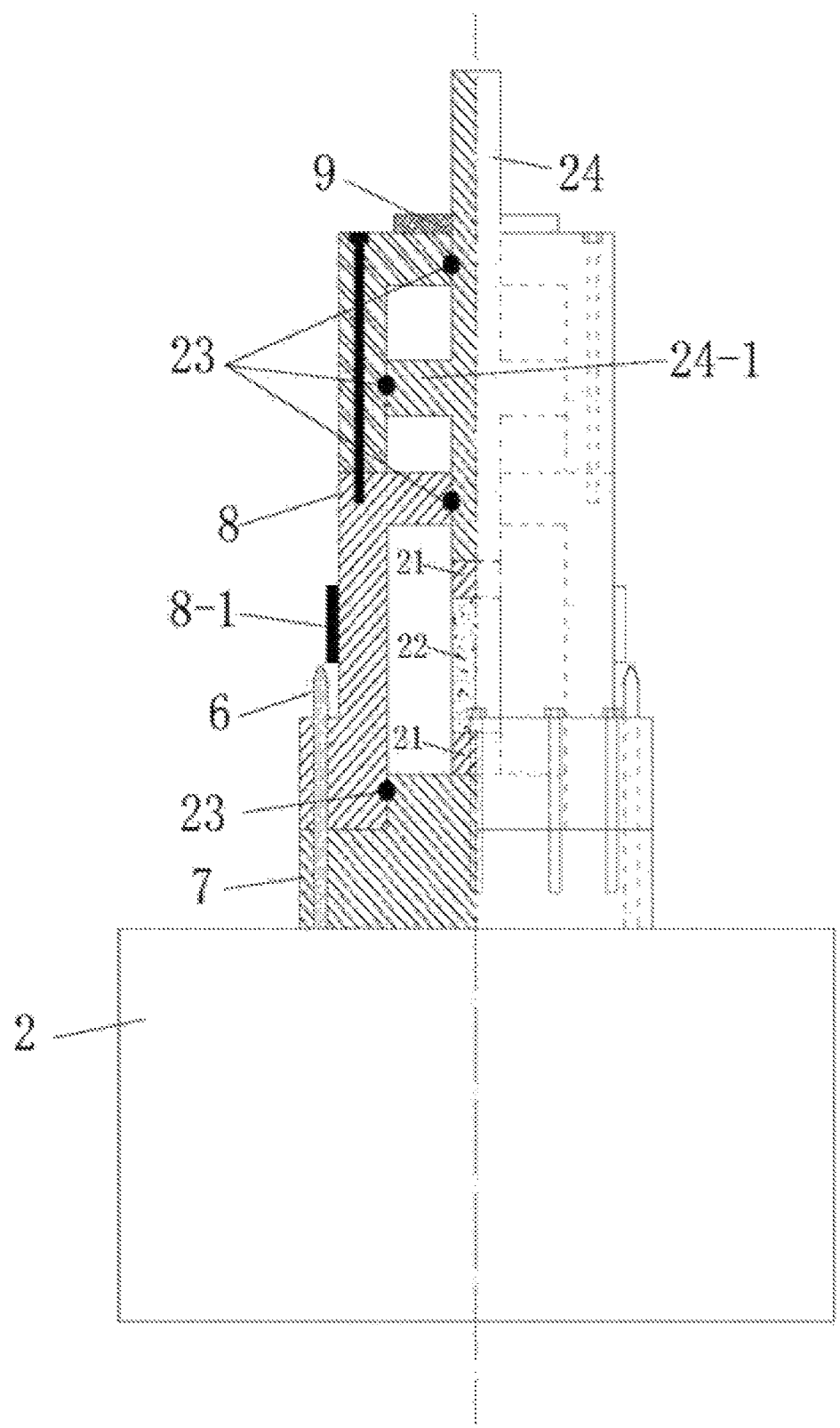
FIG. 5 is a structural diagram of a section view of A-A direction in FIG. 4.

In the drawings, each reference numeral represents: 1, door-shaped support frame; 2, base; 3, oil source; 4, conveying pipe; 5, hydraulic oil control switch; 6, centering pin; 7, test pedestal; 8, chamber cavity; 8-1, heating element; 9, coupling chassis; 10, lower lifting rod; 11, locking pin; 12, upper lifting rod; 13, locking pin rod; 14, safety disk; 15, nut; 16, fixing rod; 17 beam; 18 piston; 19, cylinder; 20, oil hydraulic rod; 21, indenter; 22, test piece; 23, seal ring; 24, axial stress loading piston shaft; 24-1, axial stress loading piston; 25, lateral stress loading controlling and testing module; 25-1, confining pressure loading and testing module; 25-2, fifth shutoff valve; 25-3, sixth shutoff valve; 25-4, volume deformation testing module; 26, axial stress loading controlling and testing module; 27, high pressure seepage field building module; 27-1, first shutoff valve; 27-2, liquid seepage field loading measurement and controlling module; 27-3, second shutoff valve; 27-4, gas seepage field building loading measurement and controlling module; 27-5, third shutoff valve; 27-6, gas pressurization module; 27-7, fourth shutoff valve; 27-8, pressure reducing valve; 27-9, gas cylinder; 28, seepage liquid permeating measurement and controlling module; 28-1, sixth shutoff valve; 28-2, liquid medium permeating or the mixed-phase medium permeating controlling and measurement module; 29, seepage gas permeating measurement and controlling module; 29-1, seventh shutoff valve; 29-2, first pressure gauge; 29-3, first automatic on-off valve; 29-4, gas storage tank; 29-5, second pressure gauge; 29-6, second automatic on-off valve.

DETAILED DESCRIPTION

The embodiments of the present invention are described below in conjunction with the drawings, and the present invention will be further described through the embodiments. The specific embodiments of the present invention are not limited to the manner described in the embodiments.

Embodiment 1

A rock mechanics experiment system for simulating a deep-underground environment of the present embodiment, includes a triaxial chamber consisting of chamber cavity 8 and test pedestal 7, a stress field building module, high pressure seepage field building module 27 and a seepage medium permeating control measurement module arranged in the triaxial chamber and connected to the triaxial chamber through pipe, heating element 8-1 disposed on the high temperature field building module in the chamber cavity of the triaxial chamber, a lifting module used for installing and disassembling of the chamber cavity, and a computer module used for controlling the operation of system and calculating and outputting the test data. The lifting module includes door-shaped support frame 1, cylinder piston device vertically mounted on the door-shaped support frame beam 17, coupling device and safety suspension device. The cylinder piston device is as follows. The rising distance of the piston 18 of the cylinder piston device is 0.8 m, and the hydraulic oil control switch 5 is disposed on the conveying pipe on the frame of the door-shaped support frame, when the rock test piece is placed in the triaxial chamber or removed from the triaxial chamber, the cylinder piston device is located directly above the triaxial chamber, and the axis of cylinder 19 is consistent with the triaxial chamber. The coupling device includes oil hydraulic rod 20 with the upper end fixedly coupled with piston 18, safety disk 14 fixedly coupled with the lower end of the hydraulic rod, and two symmetrically disposed coupling assemblies with two upper ends fixedly coupled with the safety disk and two lower ends fixedly coupled with coupling chassis 9 that is fixed on the upper end of the chamber cavity and sleeved outside axial stress loading piston shaft 24. The coupling assembly is composed of upper lifting rod 12 fixedly coupled to the safety disk at the upper end and lower lifting rod 10 fixedly coupled to the coupling chassis at the lower end and locking pin 11. The lower end of the upper lifting rod and the upper end of the lower lifting rod are in socket connection by the locking pin 11. The safety suspension device includes four fixing rods 16 and two locking pin rods 13, four fixing rods 16 are oppositely disposed on two sides of door-shaped support frame beam 17, and the lower end of the fixing rod is designed with a locking pin hole matched with the locking pin rod. Two ends of the locking pin rod are designed with threaded heads, and the two locking pin rods are respectively inserted into the locking pin holes on the lower ends of the two opposite fixing rods, and the locking pin rod and nut 15 form a thread pair through the exposed threaded heads at both ends of the locking pin rod to achieve axial fixation. The four fixing rods and the two locking pin rods constitute a hanging and carrying frame for hanging the safety disk. The stress field building module includes lateral stress loading and controlling module 25 and axial stress loading and controlling module 26. The high pressure seepage field building module includes liquid seepage field loading and controlling building module 27-2 and gas seepage field building loading measurement and controlling module 27-4, both of which share a seepage medium inlet nozzle. The seepage medium permeating measurement and controlling module includes seepage liquid permeating measurement and controlling module 28 and seepage gas permeating measurement and controlling module 29, both of which share an outlet nozzle.

The experiment operation of the rock mechanics experiment system for simulating the deep-underground environment described in this embodiment is as follows:

1. Preparation Before Test and Removal of Test Piece After Test

Figure 6:
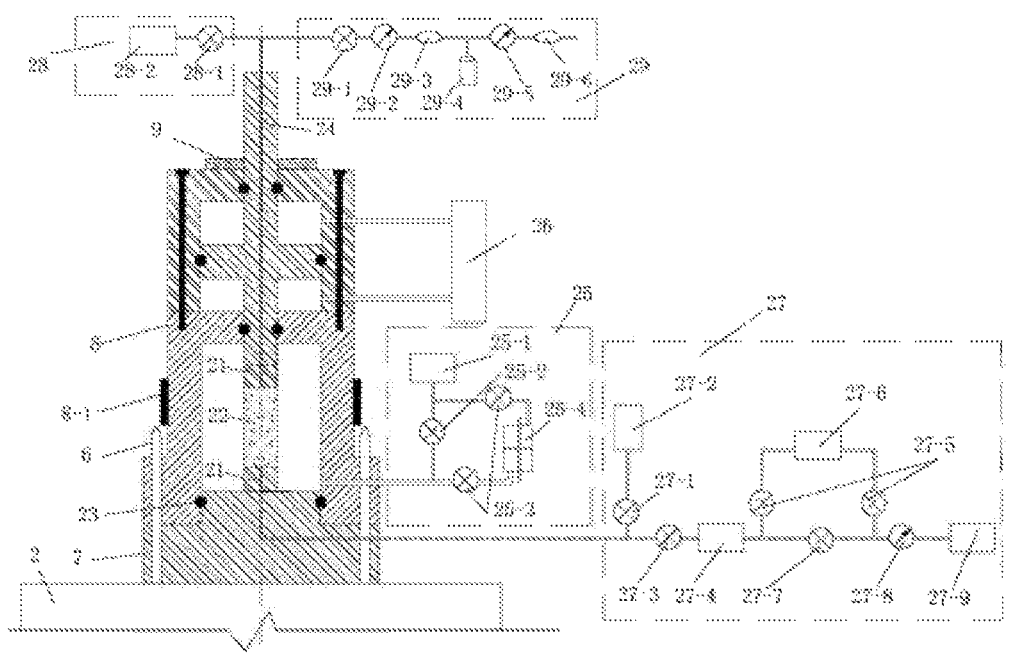
FIG. 6 is schematic diagram of a frame structure of rock mechanics experiment system of simulating deep-underground environment of the present invention.

Referring to FIG. 6, before the experiment, the prepared test piece is first placed flat in the center of test pedestal 7, and the height of axial stress loading piston shaft 24 is adjusted by axial stress loading controlling and testing module 26, so that the bottom of axial stress loading piston shaft 24 is in contact with indenter 21 at the upper part of test piece 22. Then, the locking pin rod 13 in the lifting module safety device is pulled out, hydraulic oil control switch 5 of the cylinder piston device is opened, so that chamber cavity 8 of the triaxial chamber descends slowly, and centering pin 6 on test pedestal 7 is aligned with the centering hole on the chamber cavity. After the triaxial chamber descends to a predetermined position, the lifting switch is closed, and locking pin 11 for coupling the upper lifting rod 12 with the lower lifting rod in the coupling assembly is pulled out, and the fixing bolt is tightened to fix the chamber cavity on the test pedestal, a triaxial pressure chamber for testing of rock test piece is constructed. Hydraulic oil control switch 5 of the cylinder piston device is turned on again to make the upper lifting rod in the lifting module rise to the top, and then the guide rod of the axial displacement deformation sensor that measures the deformation of the test piece is inserted into the guide rod mounting hole in the loading shaft. One end of the guide rod is in contact with indenter 21 at the upper part of the test piece, and the other end is connected to the displacement sensor fixedly mounted on the triaxial side wall through the horizontal rod at the top of the guide rod, and then confining pressure oil can be filled into the triaxial chamber through lateral stress loading controlling and testing module 25, after the confining pressure oil is full, a loading and testing test can be carried out according to the required type of test, the predetermined loading scheme and test contents.

After the test is completed, the axial load is removed by the axial stress loading controlling and testing module 26, and then after the confining pressure oil in triaxial chamber 8 is completely discharged back into lateral stress loading controlling and testing module 25, the guide rod bolt of the axial displacement deformation sensor connecting to the displacement sensor is released to remove the guide rod from the guide rod hole in the middle of loading shaft, and then the fixing bolt can be screwed out. The upper lifting rod is controlled to descend to the connection part with the lower lifting rod through the lifting switch, locking pin 11 is plugged, and the lifting switch is turned on to lift the chamber cavity of triaxial chamber to the setting height, locking pin rod 13 is inserted into the locking pin hole at the lower end of the fixing rod, so that the safety disk 14 is hanged on hanging and carrying frame formed by four fixing rods and two locking pin rods, then the test piece is taken out from test pedestal 7, and the base and the test stand are cleaned.

2. Confining Pressure Loading Operation of Confining Pressure Loading Module

When chamber cavity 8 of triaxial chamber and test pedestal 7 are fixed together by bolt, and the lifting rod rises to the top, the guide rod of the axial displacement deformation sensor for measuring the deformation of the test piece is inserted into the guide rod mounting hole of the loading shaft. One end of the guide rod is in contact with indenter 21 at the upper part of the test piece, and the other end is connected to the displacement sensor fixedly mounted on the triaxial side wall through the horizontal rod at the top of the guide rod. Then fifth shutoff valve 25-2 and sixth shutoff valve 25-3 in confining pressure loading and testing module 25-1 is turned on, the confining pressure loading and testing module 25-1 is started, the confining pressure oil is injected into the triaxial chamber, and the piston in the volume deformation testing module 25-4 is adjusted to position the piston in the middle of the cylinder. After the confining pressure oil is filled, the first shutoff valve is closed. During the test, the rock test piece is deformed under the load effect, and the deformation amount can be measured by volume deformation testing module 25-4.

3. Loading Operation of Permeating Module (1) Osmotic Medium is a Separate Liquid Medium After the above-mentioned confining pressure loading and volume deformation operations are completed, the confining pressure oil is filled, and the confining pressure is applied to the predetermined target value, the following steps can be performed. Only first shutoff valve 27-1 in high pressure seepage field building module 27 is turned on, (27-3 to 27-9 in the module are not activated), and liquid seepage field loading and controlling module 27-2 is started to control and measure the loading of the liquid medium; sixth shutoff valve 28-1 of seepage liquid permeating measurement and controlling module 28 is turned on, and the liquid medium permeating or the mixed-phase medium permeating controlling and measurement module 28-2 is started to control and measure the permeating liquid (seepage gas permeating measurement and controlling module 29 is not activated).

(2) Osmotic Medium is a Separate Gas Medium

After the above-mentioned confining pressure loading and volume deformation operations are completed, the confining pressure oil is filled, and the confining pressure is applied to the predetermined target value, the following steps can be performed. For high pressure seepage field building module 27, first shutoff valve 27-1 is closed, and liquid seepage field loading and controlling module 27-2 is not activated. If the gas permeation inlet pressure required for the test is low, only the pressure in gas cylinder 27-9 can meet the test requirements, third shutoff valve 27-5 is closed, at this time, gas pressurization module 27-6 is not activated. Second shutoff valve 27-3 and fourth shutoff valve 27-7 are turned on, and the pressure reducing valve 27-8 is adjusted to a proper scale, and then gas cylinder 27-9 can be opened. During the test, the gas seepage field building loading measurement and controlling module 27-4 is used.

If the test gas requires high pressure, fourth shutoff valve 27-7 is turned off, and second shutoff valve 27-3 and third shutoff valve 27-5 are turned on. Since the gas outputted from the gas cylinder is required to be pressurized, the scale of the pressure reducing valve 27-8 can be adjusted to maximum. After gas cylinder 27-9 is opened, gas pressurization module 27-6 is started to pressurize the gas. During the test, gas seepage field building loading measurement and controlling module 27-4 is used.

For the seepage medium permeating measurement and controlling module, seepage liquid permeating measurement and controlling module 28 is not activated during the entire test process, and only seepage gas permeating measurement and controlling module 29 is activated. During the test, the seventh shutoff valve 29-1 is turned on, and the first pressure gauge 29-2 is a small-range pressure gauge. When test pressure of the first pressure gauge reaches a predetermined value, first automatic on-off valve 29-3 is automatically turned on. After the gas between the first pressure gauge and the test piece is released to gas storage tank 29-4, the first automatic on-off valve is automatically turned off. After the first automatic on-off valve is turned on and off for several times, gas storage tank 29-4 is filled with gas of higher pressure. Second pressure gauge 29-5 is a large-range pressure gauge, and the setting scale is higher than that of the first pressure gauge. When the second pressure gauge detects that the pressure in the gas storage tank reaches a predetermined value, second automatic on-off valve 29-6 is automatically turned on, and the high pressure gas in the gas storage tank is released to the atmosphere. The test machine testing system can automatically detect and record the pressure of each pressure gauge and the number of automatic turning on of the automatic on-off valve.

(3) Osmotic Medium is a Gas-Liquid Mixed-Phase Medium

A. Simultaneous Injection of Mixed-Phase Medium:

If the gas does not require pressurization, third shutoff valve 27-5 at the gas portion of the inlet is always turned off, and gas pressurization module 27-6 is not activated. Otherwise, if pressurization is required, it needs to be activated.

When mixed-phase of the gas medium and the liquid medium is simultaneously loaded, first shutoff valve 27-1 and second shutoff valve 27-3 need to be turned on, and the gas medium and the liquid medium start to input at the same pressure and are automatically mixed in the inlet nozzle and test piece 22. Only seepage liquid permeating measurement and controlling module 28 is activated, measurement and controlling thereof are the same as those of permeating outlet when seepage medium is separate liquid medium.

B. Injection of Liquid Medium First:

Firstly, only first shutoff valve 27-1 is turned on, and the assemblies 27-3 to 27-9 in the gas seepage field loading measurement and controlling module are not activated, and liquid seepage field loading measurement and controlling module 27-2 is activated to control and measure the loading of liquid medium. After the liquid medium is injected according to the predetermined test scheme, first shutoff valve 27-1 is turned off, and the liquid seepage field loading measurement and controlling module 27-2 is turned off. Then, separate gas medium is taken as osmotic medium, of which gas medium inlet testing method is used. For the osmotic outlet, the operation is carried out as "the osmotic medium is a separate gas medium".

C. Injection of Gas Medium First:

First, the operation is carried out as the method of "osmatic medium is a separate gas medium". After the gas medium is injected according to a predetermined test scheme, second shutoff valve 27-3 is turned off. Then, the operation is carried out as the method of "the osmotic medium is a separate liquid medium". For osmotic outlet, the operation is carried out as the method of "osmotic medium is a separate gas medium".

What is claimed is:

1. A rock mechanics experiment system for simulating deep-underground environment, comprising:
    a triaxial chamber consisting of a chamber cavity and a test pedestal,
    a stress field building module, a high pressure seepage field building module and a high temperature field building module inside the triaxial chamber,
    a seepage medium permeating measurement and controlling module,
    a lifting module used for installing and disassembling the chamber cavity, and
    a computer measurement and controlling module; wherein
    the lifting module comprises a door-shaped support frame, a cylinder piston device vertically installed on a beam of the door-shaped support frame, a coupling device and a safety suspension device; the coupling device comprises an oil hydraulic rod with an upper end fixedly connected to a piston of the cylinder piston device, a safety disk fixedly connected to a lower end of the oil hydraulic rod, and two coupling assemblies arranged symmetrically with upper ends fixedly connected to the safety disk and lower ends fixedly connected to an upper end of the chamber cavity, each of the coupling assemblies consists of an upper lifting rod with an upper end fixedly connected to the safety disk, a lower lifting rod with a lower end fixedly connected to the upper end of the chamber cavity and a locking pin; a lower end of the upper lifting rod and an upper end of the lower lifting rod are connected through the locking pin in a socket way; the safety suspension device comprises four fixing rods and two locking pin rods, the four fixing rods are fixed on the beam of the door-shaped support frame through an upper end and are arranged opposite to one another in pairs, a lower end of each of the fixing rods is provided with a locking pin hole matched with the locking pin in the socket way; the two locking pin rods are respectively inserted into the locking pin holes on lower end parts of the four fixing rods oppositely arranged and are axially fixed, and the four fixing rods and the two locking pin rods form a hanging and carrying frame for suspending the safety disk.

2. The rock mechanics experiment system for simulating deep-underground environment according to claim 1, wherein the four fixing rods are respectively and oppositely fixed on both sides of the beam of the door-shaped support frame.

3. The rock mechanics experiment system for simulating deep-underground environment according to claim 1, wherein each of the locking pin rods is designed with an axial positioning structure to prevent a failure of the hanging and carrying frame consisting of the four fixing rods and the two locking pin rods.

4. The rock mechanics experiment system for simulating deep-underground environment according to claim 3, wherein the axial positioning structure is a thread pair formed by a screw thread and a nut on an outer end of each of the locking pin rods.

5. The rock mechanics experiment system for simulating deep-underground environment according to claim 1, wherein the upper end of the chamber cavity is fixedly provided with a coupling chassis, the coupling chassis is designed with an installing hole sleeved with an axial stress loading piston shaft, and the lower end of the lower lifting rod in each of the coupling assemblies is fixedly connected to the coupling chassis.

6. The rock mechanics experiment system for simulating deep-underground environment according to claim 1, wherein a distance of a rising stroke of the piston of the cylinder piston device is more than 0.40 meters.

7. The rock mechanics experiment system for simulating deep-underground environment according to claim 6, wherein a hydraulic oil control switch of the cylinder piston device is arranged on a conveying pipe positioned on a vertical frame of the door-shaped support frame.

8. The rock mechanics experiment system for simulating deep-underground environment according to claim 1, wherein the stress field building module comprises a lateral stress field loading measurement and controlling module and an axial stress field loading measurement and controlling module.

9. The rock mechanics experiment system for simulating deep-underground environment according to claim 1, wherein the high pressure seepage field building module comprises a liquid seepage field building loading measurement and controlling module and a gas seepage field building loading measurement and controlling module; the seepage medium permeating measurement and controlling module comprises a seepage liquid permeating measurement and controlling module and a seepage gas permeating measurement and controlling module.

10. The rock mechanics experiment system for simulating deep-earth environment according to claim 9, wherein the liquid seepage field building loading measurement and controlling module and the gas seepage field building loading measurement and controlling module share one seepage medium inlet connection pipe, and the seepage liquid permeating measurement and controlling module and the seepage gas permeating measurement and controlling module share one outlet connection pipe.

11. The rock mechanics experiment system for simulating deep-underground environment according to claim 2, wherein the upper end of the chamber cavity is fixedly provided with a coupling chassis, the coupling chassis is designed with an installing hole sleeved with an axial stress loading piston shaft, and the lower end of the lower lifting rod in each of the coupling assemblies is fixedly connected to the coupling chassis.

12. The rock mechanics experiment system for simulating deep-underground environment according to claim 3, wherein the upper end of the chamber cavity is fixedly provided with a coupling chassis, the coupling chassis is designed with an installing hole sleeved with an axial stress loading piston shaft, and the lower end of the lower lifting rod in each of the coupling assemblies is fixedly connected to the coupling chassis.

13. The rock mechanics experiment system for simulating deep-underground environment according to claim 4, wherein the upper end of the chamber cavity is fixedly provided with a coupling chassis, the coupling chassis is designed with an installing hole sleeved with an axial stress loading piston shaft, and the lower end of the lower lifting rod in each of the coupling assemblies is fixedly connected to the coupling chassis.

14. The rock mechanics experiment system for simulating deep-underground environment according to claim 2, wherein a distance of a rising stroke of the piston of the cylinder piston device is more than 0.40 meters.

15. The rock mechanics experiment system for simulating deep-underground environment according to claim 3, wherein a distance of a rising stroke of the piston of the cylinder piston device is more than 0.40 meters.

16. The rock mechanics experiment system for simulating deep-underground environment according to claim 4, wherein a distance of a rising stroke of the piston of the cylinder piston device is more than 0.40 meters.

17. The rock mechanics experiment system for simulating deep-underground environment according to claim 14, wherein a hydraulic oil control switch of the cylinder piston device is arranged on a conveying pipe positioned on a vertical frame of the door-shaped support frame.

18. The rock mechanics experiment system for simulating deep-underground environment according to claim 15, wherein a hydraulic oil control switch of the cylinder piston device is arranged on a conveying pipe positioned on a vertical frame of the door-shaped support frame.

19. The rock mechanics experiment system for simulating deep-underground environment according to claim 16, wherein a hydraulic oil control switch of the cylinder piston device is arranged on a conveying pipe positioned on a vertical frame of the door-shaped support frame.

20. The rock mechanics experiment system for simulating deep-underground environment according to claim 2, wherein the stress field building module comprises a lateral stress field loading measurement and controlling module and an axial stress field loading measurement and controlling module.

* * * * *